United States Patent [19]

Patel

[11] 4,335,723
[45] * Jun. 22, 1982

[54] CATHETER HAVING INFLATABLE RETENTION MEANS

[75] Inventor: Bhupendra C. Patel, Elgin, Ill.

[73] Assignee: The Kendall Company, Boston, Mass.

[*] Notice: The portion of the term of this patent subsequent to Oct. 10, 1995, has been disclaimed.

[21] Appl. No.: 929,948

[22] Filed: Jul. 31, 1978

Related U.S. Application Data

[63] Continuation of Ser. No. 745,098, Nov. 26, 1976, abandoned.

[51] Int. Cl.³ ............................................. A61M 25/00
[52] U.S. Cl. ................................................ 128/349 B
[58] Field of Search .............. 128/348, 349 R, 349 B, 128/349 BV, 350, 351; 260/880 B

[56] References Cited

U.S. PATENT DOCUMENTS

| | | | |
|---|---|---|---|
| 3,363,629 | 1/1968 | Kuhn | 128/351 |
| 3,395,710 | 8/1968 | Stratton et al. | 128/350 R |
| 3,485,787 | 12/1969 | Haefele | 260/880 B |
| 3,543,759 | 12/1970 | McWhorter | 128/349 BV |
| 3,606,669 | 9/1971 | Kemble | 128/351 |
| 3,850,720 | 11/1974 | Collins | 128/349 R |
| 3,865,776 | 2/1975 | Gergen | 260/33.6 AQ |
| 3,896,815 | 7/1975 | Fettel et al. | 128/348 |
| 4,093,484 | 6/1978 | Harrison et al. | 128/349 B |
| 4,119,099 | 10/1978 | Patel | 128/349 R |

FOREIGN PATENT DOCUMENTS

| | | | |
|---|---|---|---|
| 2188448 | 1/1974 | France | 128/349 R |
| 1234037 | 6/1971 | United Kingdom . | |

*Primary Examiner*—E. H. Eickholt

[57] ABSTRACT

A catheter having a shaft carrying an inflatable retention means such as a Foley indwelling or retention catheter or an endotracheal tube is provided with a retention balloon or bulb comprising thermoplastic elastomer in the form of a sleeve or collar having its margins bonded to the outer surface of the shaft which maintains its inflation and its retention capability for an extended period of time. When the catheter shaft is made of thermoplastic elastomer, the balloon can be heat sealed to the shaft. A one-piece connector including drainage fitting, inflation side arm and safety signal balloon can be bonded to the proximal end of the shaft.

18 Claims, 5 Drawing Figures

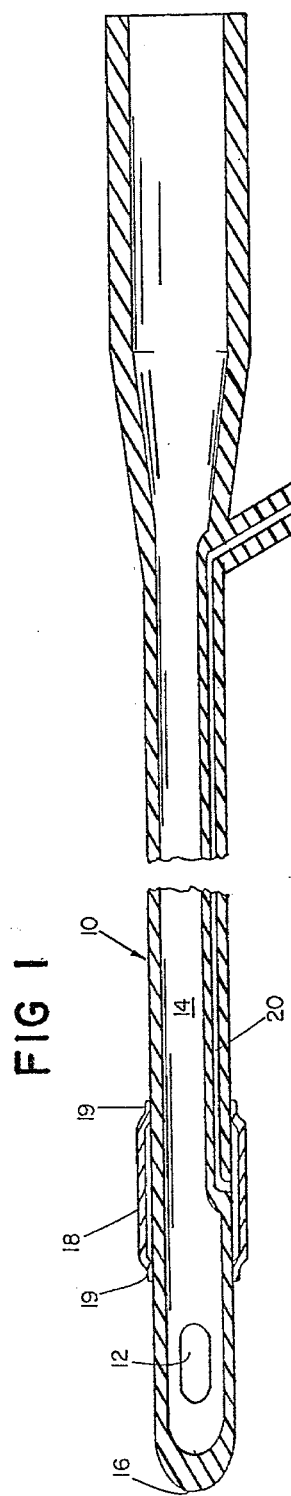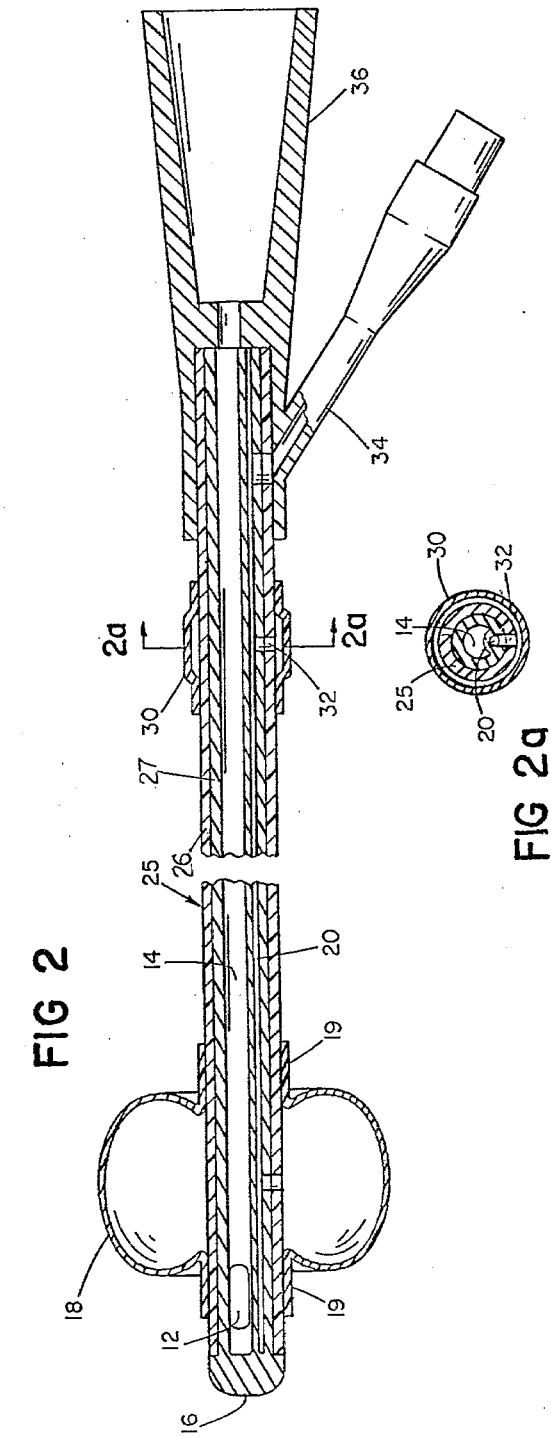
FIG 1
FIG 2
FIG 2a

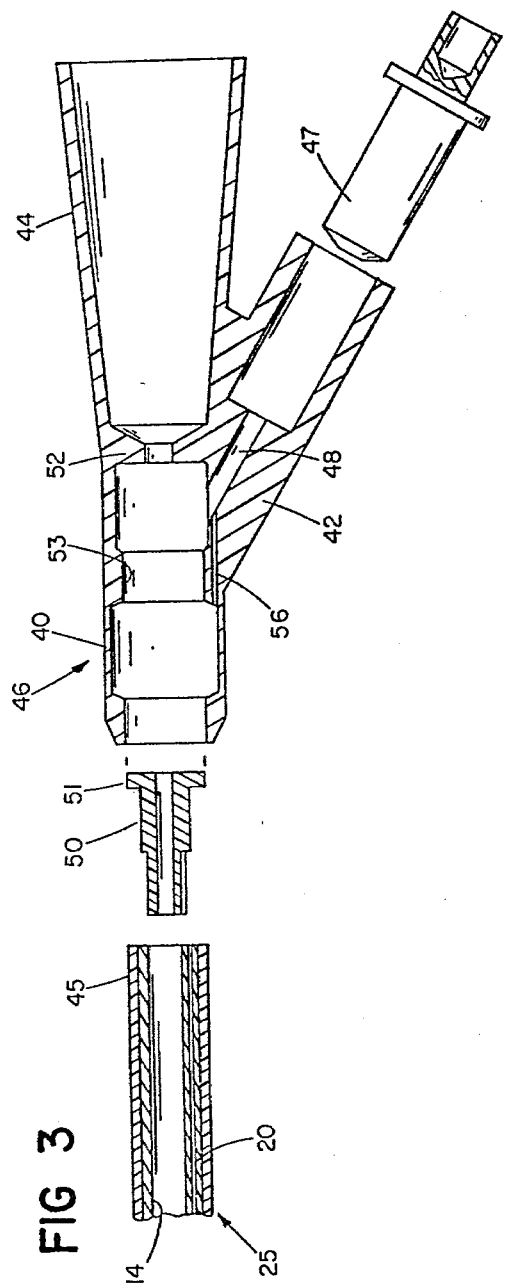
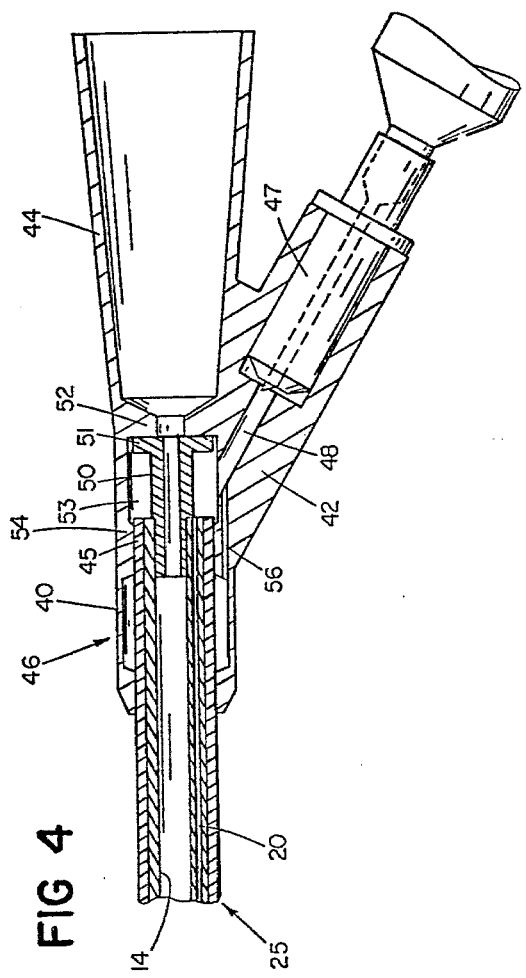

CATHETER HAVING INFLATABLE RETENTION MEANS

This is a continuation of application Ser. No. 745,098 filed Nov. 26, 1976 now abandoned.

This invention relates to a catheter having a shaft carrying an inflatable retention means, such as a Foley indwelling or retention catheter or an endotracheal tube and pertains more specifically to such a catheter in which the retention means comprises a balloon having a wall consisting essentially of a thermoplastic elastomer which is a block polymer including a thermoplastic polystyrene end block and an elastomeric saturated open chain hydrocarbon polymer block. It also pertains to a Foley catheter having a safety signal balloon of such thermoplastic elastomer which is molded as a part of a connector unit including a drainage fitting and an inflation side arm, the unit being bonded to the proximal end of the catheter.

Foley indwelling or retention catheters, that is, urinary catheters, are constructed with an elastic inflatable balloon surrounding the catheter shaft near the distal end. The balloon in deflated condition snugly engages the shaft so that it impedes as little as possible insertion of the catheter shaft through the urethra until its drainage eye reaches the desired position, e.g., in the bladder, whereupon the balloon is inflated through a separate inflation lumen passing through the shaft; the inflation medium usually is water, normal saline, or glucose solution. The inflation lumen is sealed with the balloon in inflated condition to prevent withdrawal of the catheter. In normal usage, such a catheter remains in position for an extended period of time ranging from hours to as much as several weeks, during all of which time the retention balloon must remain inflated to ensure that the catheter is not accidentally withdrawn. At the time withdrawal is desired, the seal is released, the inherent elasticity of the balloon wall causing the balloon to collapse to its original uninflated condition snugly engaging the shaft with accompanying ejection of the inflation medium through its lumen. Endotracheal tubes also have an inflatable balloon surrounding the shaft of the tube near the distal end serving as a retention and sealing bulb or cuff. Endotracheal tubes are used primarily during surgery to control the nature and quantity of air and other gases inhaled and exhaled by the patient, the tube being inserted by endotracheal intubation; the tube can also be inserted after tracheotomy.

In the case of both Foley catheters and endotracheal tubes, the retention balloons or bulbs have hitherto been made of natural (latex) rubber or of silicone rubber. In the case of the Foley catheter, such balloons tend to become deflated during use by diffusion of the inflation liquid, usually water, through the wall necessitating frequent pressure measurements and reinflation to ensure proper functioning. In the case of endotracheal tubes such bulbs have required high inflation pressures of the order of 50 mm. of water, which, together with the inherent biologically irritating nature of the rubber has given rise to the problem of necrosis of the tracheal tissue in the area of contact of the bulb. Retention balloons have also hitherto been made of thermoplastic materials such as polyethylene or plasticized polyvinyl chloride. However, in the case of Foley catheters, such retention balloons have been unsuccessful because of the lack of elasticity of the material and the consequent inability of the balloon to resume its original uninflated size and shape after deflation. In the case of endotracheal tubes, such bulbs made of thermoplastic materials, even when made oversize, having an uninflated diameter greater than that of the trachea, so that they are flaccid when inflated to bring them into sealing engagement with the trachea, have required close attention and frequent reinflation because of the diffusion of air and/or anesthetic gases such as nitrous oxide through the wall of the bulb.

The present invention of a catheter having a shaft carrying an inflatable retention means comprising a balloon or bulb having a wall composed of thermoplastic elastomer makes it possible to employ a balloon or bulb which can be very thin walled with minimal loss of its inflation-maintaining properties because of diffusion of water through the wall and which can also be inflated at low pressure. Such a catheter also displays minimal diffusion of air and anesthetic gases through the wall of the bulb, so that both Foley catheters and endotracheal tubes made in accordance with this invention are greatly superior to those of the prior art. In addition, the present invention provides a novel connector construction including both an inflation side arm and a safety signal balloon in a one-piece unit adapted for easy mounting on the end of an extruded shaft containing an inflation lumen as a part of its wall.

The present invention also provides a catheter having a shaft carrying an inflatable retention means comprising a balloon having a wall of elastic material, said shaft being a coextruded laminate in which the outer lamination is capable of being bonded to said balloon. By selecting the material of the outer lamination to be compatible with the elastic material of the balloon wall or compatible with an adhesive which bonds effectively to the balloon wall, the balloon and shaft are readily bonded together either by heat sealing or by a layer of adhesive, as the case may be. The very large area of contact between the outer and inner laminations of the coextruded shaft ensures firm connection of the two by mechanical or frictional interlock even though the two materials are not compatible, i.e., cannot be firmly bonded by heat sealing or by an intervening adhesive material.

It has previously been proposed in Fettel et al. U.S. Pat. No. 3,896,815 to make an embolectomy catheter and its balloon from thermoplastic elastomer. However, the balloons of embolectomy catheters are inflated only during withdrawal of the catheter, during which operation they serve to engage the embolisms present in the blood vessel so that the latter are withdrawn along with the catheter. The time period during which the balloon of an embolectomy catheter must remain inflated is only of the order of a few minutes at most.

It has also been proposed in Buckles et al. U.S. Pat. No. 3,817,248 to provide a drug delivery device for insertion into a body cavity in the form of a catheter having mounted on its distal end an inflated balloon containing a drug under pressure, the drug being dispensed through a suitable orifice over a long period of time by the pressure exerted by the balloon as it deflates. The patent describes such a device in which the shaft of the catheter may be made of Kraton polymer, a trademark for a thermoplastic elastomer. Kraton polymer has been described by its supplier as having features which should make it suitable for making catheters among other products.

It has now been found that catheters having unique advantages are provided when the retention balloon or bulb has a wall consisting essentially of thermoplastic elastomer comprising a block polymer in the form of an end block of styrene polymer and an elastomeric block of saturated open chain hydrocarbon polymer. The elastomeric saturated hydrocarbon polymer block can be hydrogenated rubbery polybutadiene or a polyolefin rubber such as an ethylene-butylene copolymer. Particularly preferred are block polymers in which two end blocks are of polystyrene and the center block is elastomeric as described above. Thermoplastic elastomer commercially available under the name Kraton G-1650 and Kraton G-1652 can be used. The material forming the wall of the retention balloon or bulb normally contains, in addition to the block polymer itself, conventional compounding ingredients including plasticizing oils such as paraffinic oils (mineral oil), stiffening agents such as polypropylene, and antidegradants to provide stability during processing and protection against aging, such compounded material being commercially available under the name Kraton G-2705 containing 20 to 40% by weight of block polymer and the balance conventional compounding ingredients.

The balloon or bulb can best be made separately from the remainder of the catheter by injection molding or blow molding a tube of the desired dimensions and wall thickness which is cut to length to provide a collar or sleeve capable of being slipped over the shaft or tube of the catheter and capable of being bonded thereto along the margins of the collar or sleeve by an appropriate adhesive. In a preferred embodiment of the Foley catheter, the shaft is made of material consisting essentially of a thermoplastic elastomer, which can be identical to the one from which the collar or sleeve is made if desired; the shaft can also be made of any other material of which Foley catheter shafts are conventionally made such as natural rubber, silicone or other desired synthetic rubber, or suitable thermoplastic materials such as plasticized polyvinylchloride or polyurethane. In a preferred embodiment of the endotracheal tube, the shaft is made in whole or in part of a relatively stiff material such as plasticized polyvinylchloride, polyurethane, polyolefin, e.g., polyethylene or polypropylene, synthetic rubber, or the like. Preferably the shaft of the endotracheal tube is of laminated construction in which the inner lamination or core is made of material which is substantially stiffer than the thermoplastic elastomer material of which the wall of the bulb is made, and the outer lamination or covering for the core consists essentially of thermoplastic elastomer material which is a block polymer including a thermoplastic polystyrene end block and an elastomeric saturated open chain hydrocarbon block the thermoplastic elastomer material may be identical to the one from which the wall of the bulb is made. When the catheter shaft is made wholly of thermoplastic material, whether a thermoplastic elastomer or not, having a softening point approximately the same as (preferably ±10° C.) that of the thermoplastic elastomer material of which the wall of the retention balloon or bulb is made, the latter can be bonded along its margins to the shaft by heat-sealing or welding without the necessity of using any separate adhesive. In the case in which the shaft is of laminated construction in which the core or inner laminations are composed of material different from that of the outer lamination to provide more desirable physical properties such as stiffness for the shaft as a whole, these inner laminations need not have a softening point close to that of the material of which the balloon or bulb is made, but the outer lamination should have such a softening point in order to permit heat sealing of the margins of the sleeve or collar to the surface of the shaft. However, any conventional effective adhesive in liquid or solution form may be used if desired for effective bonding of the balloon or bulb to the shaft. The large area of the surfaces of inner and outer laminations in contact with each other provides sufficient physical interference, particularly when the shaft is formed by simultaneous coextrusion of the laminations in intimate contact with each other as they are formed in the extrusion die, so that no added adhesive and no closeness of softening point is required in order to obtain adequate bonding of the laminations to each other.

In the drawing:

FIG. 1 is a view in side elevation, partly broken away and in section of one embodiment of a Foley catheter of the present invention;

FIG. 2 is a view in side elevation, partly broken away and in section, showing a second embodiment of a Foley catheter of the invention having a safety signal balloon near the proximal end and showing the retention balloon in inflated condition;

FIG. 2a is a cross-sectional view taken along line 2a—2a of FIG. 2;

FIG. 3 is a view in section of the proximal end of a third embodiment of a Foley catheter of the invention in which the shaft and end fitting are constructed separately, shown before assembly;

FIG. 4 is a view in section showing the proximal end of the embodiment of FIG. 3 in assembled position.

Figure 5:
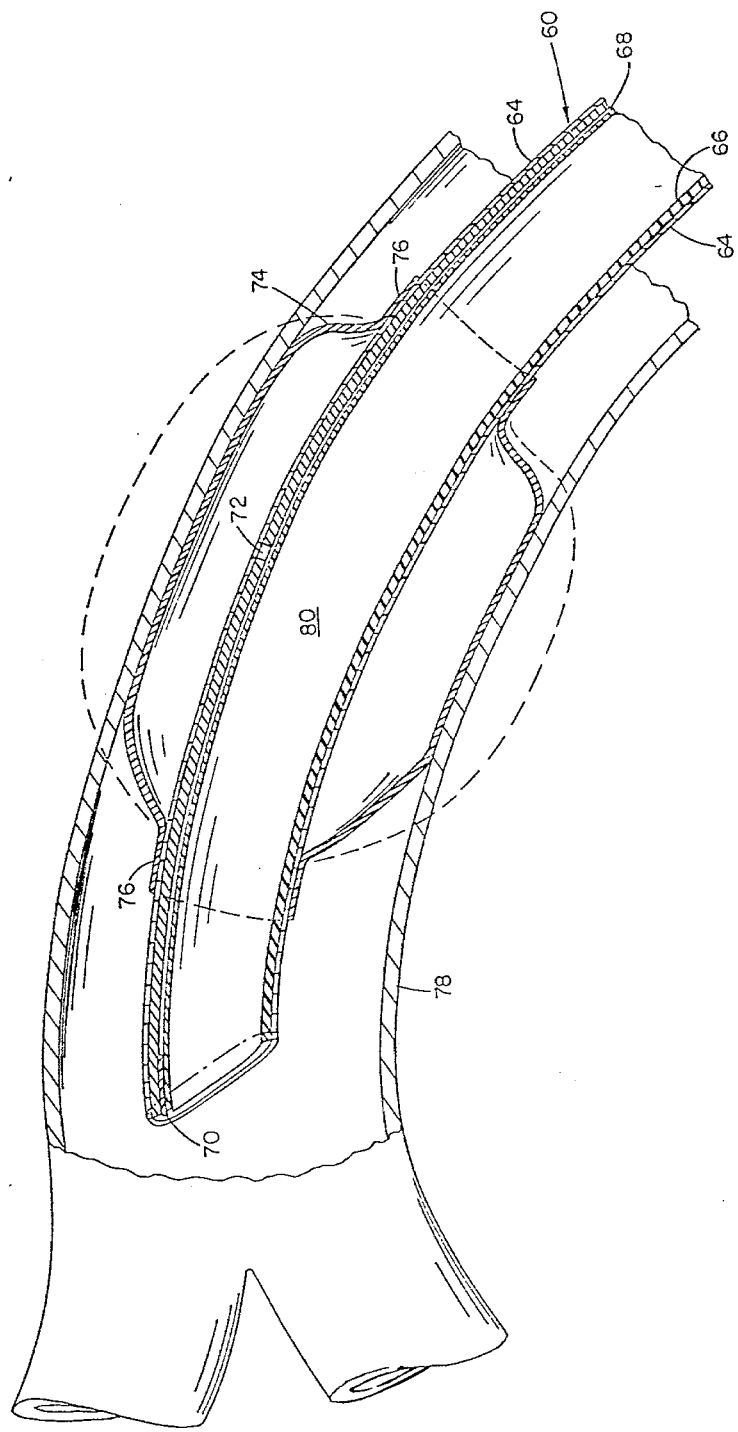
FIG. 5 is a view in section showing one embodiment of an endotracheal tube of the present invention in place within a trachea.

In the embodiment shown in FIG. 1 of the drawing, shaft 10 of the Foley retention catheter is provided with a drainage eye 12 near its distal end which communicates with the drainage or main lumen 14 extending throughout the length of shaft 10. A tip 16 is sealed in place at the distal end of the catheter shaft to close the end of lumen 14. Retention balloon 18 is provided in the form of a sleeve fitting closely over the catheter shaft adjacent its distal end with the interior of the balloon in communication with inflation lumen 20. Side arm 22 is provided near the proximal end of catheter shaft 10 giving separate access to the inflation lumen. The side arm 22 includes a plug 24 serving as a combination filling plug and stopper closes the end of the inflation lumen 20, while shaft 10 is adapted to be connected to a conventional collection device (not shown). The sleeve forming balloon 18 is made by extruding or molding in the form of a tube the desired thermoplastic elastomer, such as that sold under the trademark Kraton 2705, a block copolymer having polystyrene end blocks and a center block of polyolefin rubber in combination with a naphthenic (mineral) oil and an antidegradant. The inside diameter of balloon 18 in the uninflated condition is such that it is a snug fit over the outer surface of shaft 10. The margins 19 of balloon 18 are bonded to shaft 10 by applying a conventional Kraton adhesive composition, or, in the preferred embodiment in which shaft 10 is itself composed of Kraton 2705 thermoplastic elastomer material and made by extrusion, by heat sealing the margins 19 of balloon 18 to shaft 10. In the latter case, the seal is preferably made so that the thickness of the balloon wall in the margin 19 tapers or decreases toward the ultimate edge of the balloon sleeve, as appears in FIG. 1, thus facilitating insertion and removal of the catheter.

Retention balloon 18 has a wall thickness from 6 to 25 mils, while shaft 10 has a wall thickness from 20 to 80 mils, the wall thickness of inflation lumen 20 including side arm 22 being substantially greater than that of the retention balloon so that the latter will expand when pressure is applied through inflation lumen 20 by inserting the needle of a syringe through plug 24 and injecting under pressure the usual water, normal saline, or glucose solution.

The construction of the present invention is particularly advantageous when the Foley catheter, as shown in FIG. 2, has a shaft 25 which has an outer lamination 26 comprising a thermoplastic elastomer material such as Kraton 2705 coextruded with a core 27 comprising a polyolefin stiffer than Kraton 2705. This embodiment includes an external safety signal balloon 30 adjacent the proximal end of the catheter shaft 25. Signal balloon 30 is constructed in the same manner as retention balloon 18 by extruding or injection molding a tube of desired size and wall thickness, cutting off a short length of the tube to form a sleeve which is slipped over shaft 25 to the desired location where its interior communicates through hole 32 with inflation lumen 20, and sealing the sleeve in place along both of its margins by heat sealing. The pressure required to inflate a balloon, according to the Law of Laplace, is proportional directly to its tangential tension and inversely to its transverse radius and its longitudinal radius. If the wall thickness and diameter of balloon 20 is the same as that of retention balloon 18, the tangential tension of both is also the same. If both balloons have the same diameter and are mounted on the same shaft, the transverse radius (measured from the center of the shaft) of each is the same. Consequently, the balloon having the smaller longitudinal radius (measured lengthwise of the shaft from one margin of the balloon to the other) will require a greater inflation pressure. Because of the close control which is possible over the wall thickness and uniformity of balloons made in this manner from thermoplastic elastomer, it is possible to insure that balloon 30 inflates at a pressure of no more than 11-12 psi, slightly below the 13 psi inflation pressure at which tearing of the urethra is likely to take place if balloon 18 is accidentally inflated while confined in the urethra. In this construction the length of safety signal balloon 30 is less than that of balloon 18, thus insuring that retention balloon 18 will inflate at a lower pressure than will signal balloon 30 when both are unconfined, as for example when balloon 18 is properly located in the bladder. In this embodiment, side arm 34 and drainage fitting 36 are formed as separate elements and secured to shaft 25 by heat sealing or with adhesive.

In still another embodiment of the Foley catheter of the invention as shown in FIGS. 3 and 4, the safety signal balloon 40, inflation sidearm 42, and drainage fitting 44, are all molded as a single unit or connector 46 from thermoplastic elastomer and bonded to the proximal end of shaft 25. By making the unit by a molding operation, for example by injection molding, it is possible to control very closely the dimensions of the connector, particularly the wall thickness of balloon 40. In this embodiment the distal end of the Foley catheter is identical to that shown in FIG. 2, the shaft 25 being cut off at 45 for assembly with the unit 46 as described below. A combination filler plug and stopper or valve 47 is provided to close the end of passageway 48 in inflation sidearm 42. Sidearm 42 also includes a molded passageway 56 from inflation lumen 48 to the interior of signal balloon 40 so that sidearm 42 provides communication both with the interior of balloon 40 and with the centerbore of unit 46.

Connector 46 can be assembled with shaft 25 by means of rigid adapter tube 50, molded of polystyrene, polypropylene, or the like, the forward end of which fits snugly within drainage lumen 14 at end 45 of shaft 25, and the rearward end of which is provided with a flange 51 which seats against inwardly extending shoulder 52 of drainage fitting 44. The centerbore 53 of connector 46 has a diameter at its forward end 54 which provides a snug fit on the outside of shaft 25.

When the unit 46 and shaft 25 are assembled as shown in FIG. 4 with the flange 51 of adapter tube 50 seated against shoulder 52, the drainage lumen 14 is sealed from inflation lumen 48 in sidearm 42 and also from centerbore 53 by means of adapter tube 50 through which drainage lumen 14 communicates with the interior of drainage fitting 44. Inflation lumen 20 of shaft 25 communicates with centerbore 53 and thence with passageway 48 of inflation sidearm 42. After assembly the forward margin of signal balloon 40 is heat sealed to the outer surface of shaft 25. The rear margin of balloon 40 usually need not be heat sealed since the pressure in the interior of the balloon is equal to that in centerbore 53.

Adapter tube 50 being rigid rather than elastic provides improved internal support for proximal end 45 of shaft 25 and insures an adequate seal between the wall of the forward end 54 of the centerbore and the outer surface of shaft 25 which overlie the forward end of adapter tube 50. If desired an adhesive may be provided to insure a positive seal between the forward end 54 of the centerbore and end 45 of shaft 25, or a heat sealing step may be included after assembly to heat seal unit 46 to the end 45 of shaft 25 as in the case of retention balloon 18.

The operation of the assembled device shown in FIG. 4 is the same as that of the device of FIG. 2, the wall thickness of balloon 40 placing an upper limit on the pressure which can be applied to the interior of retention balloon 18; when this pressure is exceeded, signal balloon 40 inflates indicating to the user that the retention balloon is improperly located. As in the device of FIG. 2, the difference in length and wall thickness between retention balloon 18 and safety signal balloon 40 insures that the latter will not inflate when the former is properly located within the desired body cavity and unconfined during inflation.

In the embodiment shown in FIG. 5, shaft 60 of an endotracheal tube provided with a conventional opening 62 at its distal end is of laminated construction, outer lamination 64 comprising a thermoplastic elastomer material such as Kraton 2705 coextruded with an inner lamination or core 66 comprising a polyolefin such as polyethylene stiffer than Kraton 2705. Shaft 60 is provided with inflation lumen 68 in its wall during coextrusion of the tube shaft. Lumen 68 is sealed by a plug 70 at the distal end of the shaft, and an opening 72 spaced from the distal end is provided in the outer wall of the shaft communicating with lumen 68. An inflatable bulb or balloon 74 is in the form of a cuff fitting over shaft 60 having its margins 76,76 sealed or bonded to the outer surface of the shaft with the interior of the cuff in communication with inflation lumen 68 through opening 72. The outside diameter of cuff 74 is preferably greater in its unstretched but fully expanded condition as shown by broken lines in FIG. 5 than that of trachea 78 within which the endotracheal tube is to be used, in order to minimize the pressure required to seal the cuff to the trachea and minimize possible tissue damage. Cuff 74 is made from the same material and in the same way as balloon 18, its wall having a thickness from 2 to 15 mils, and its margins 76,76 are bonded to the external surface of lamination 64 by heat sealing. The proximal end (not shown) of shaft 60 may be provided with any conventional connector.

The endotracheal tube is used by inserting or intubating it into the trachea with the cuff 74 collapsed against the outside of shaft 60. The cuff is then inflated with air to press its outer surface gently against the inner wall of the trachea so that the tube is retained in position and so that the trachea is completely sealed except for the main lumen or passageway 80 through shaft 60. Deflation of the cuff permits easy removal of the tube.

What is claimed is:

1. A catheter having a shaft at least the outer surface of which consists essentially of a thermoplastic elastomer which is a block polymer including a thermoplastic polystyrene end block and an elastomeric saturated open chain hydrocarbon block, said shaft carrying an inflatable retention means comprising a balloon in the form of a sleeve having a single-layer wall of substantially uniform thickness consisting essentially of a thermoplastic elastomer which is a block polymer including a thermoplastic polystyrene end block and an elastomeric saturated open chain hydrocarbon block, said sleeve fitting closely over said shaft and having its margins bonded circumferentially to the outer surface of said shaft.

2. A catheter as claimed in claim 1 which is a Foley retention catheter and in which said block polymer includes two of said end blocks and said elastomeric block is a center block.

3. A catheter as claimed in claim 1 in which said shaft is a coextruded laminate in which the outer lamination comprises a thermoplastic material having a softening point approximately the same as that of said balloon wall, and said balloon is heatsealed to said outer lamination.

4. A catheter as claimed in claim 3 which is an endotracheal tube.

5. A catheter as claimed in claim 3 which is a Foley retention catheter.

6. A catheter as claimed in claim 4 in which said outer lamination consists essentially of a thermoplastic elastomer which is a block polymer including a thermoplastic polystyrene end block and an elastomeric saturated open chain hydrocarbon block.

7. A catheter as claimed in claim 6 in which said shaft has an inner lamination of material substantially stiffer than said outer lamination.

8. A catheter as claimed in claim 5 in which said outer lamination consists essentially of a thermoplastic elastomer which is a block polymer including a thermoplastic polystyrene end block and an elastomeric saturated open chain hydrocarbon block.

9. A Foley retention catheter having a shaft at least the outer surface of which consists essentially of a thermoplastic elastomer which is a block polymer including a thermoplastic polystyrene end block and an elastomeric saturated open chain hydrocarbon block, said shaft carrying a safety signal balloon in the form of a sleeve having a single-layer wall of substantially uniform thickness consisting essentially of a thermoplastic elastomer which is a block polymer including a thermoplastic polystyrene end block and an elastomeric saturated open chain hydrocarbon block; said sleeve having its margins bonded circumferentially to the outer surface of said shaft.

10. In a catheter having a shaft including a main lumen communicating with an opening adjacent its distal end and a separate inflation lumen, the improvement wherein said shaft carries an inflatable retention means comprising a balloon having a wall of elastic material, said shaft being a coextruded laminate in which the outer lamination is thermoplastic elastomer capable of being bonded to said balloon.

11. A balloon-type catheter which comprises a tubular shaft and an inflatable balloon member, carried by said catheter, said shaft and balloon member being made of an elastic composition which comprises essentially a block copolymer having thermoplastic rubber characteristics with a central rubbery polyolefin block and terminal blocks of polystyrene, said composition optionally including polypropylene, said formulation being mixed with sufficient hydrophobic oil-type plasticizer to provide the desired degree of softness to said elastic composition, said balloon member being sealed in position on said shaft.

12. The balloon-type catheter of claim 11 which carries a molded, branched connector at its distal end attached to said tubular shank, said branched connector being made of said elastic composition.

13. The balloon-type catheter of claim 12 in which the formulation for said shaft contains polypropylene.

14. The catheter of claim 11, in which said central rubbery polyolefin block is an ethylene-butylene copolymer.

15. The catheter of claim 12, in which said central rubbery polyolefin block comprises approximately 70 percent by weight of the copolymer molecule.

16. A catheter having a shaft at least the outer surface of which consists essentially of a thermoplastic elastomer which is a block polymer including a thermoplastic polystyrene end block and an elastomeric saturated open chain hydrocarbon block, said shaft carrying an inflatable retention means comprising a balloon in the form of a sleeve having a single-layer wall of substantially uniform thickness consisting essentially of a thermoplastic elastomer which is a block polymer including a thermoplastic polystyrene end block and an elastomeric saturated open chain hydrocarbon block, said sleeve fitting closely over said shaft and having its margins bonded circumferentially to the outer surface of said shaft, said catheter comprising in addition a safety signal balloon inflatable at a higher pressure than said retention balloon, the wall of said safety signal balloon consisting essentially of the same thermoplastic elastomer as the wall of said retention balloon, said safety signal balloon having its margins bonded circumferentially to said shaft.

17. A catheter as claimed in claim 16 in which said safety signal balloon is part of a molded connector unit including a drainage fitting, an inflation side arm, and a passageway communicating between said inflation sidearm and the interior of said balloon, said connector unit including said balloon being bonded to the proximal end of said shaft.

18. A catheter as claimed in claim 17 in which said shaft is a coextruded laminate in which the outer lamination comprises a thermoplastic material having a softening point approximately the same as that of said balloon wall, and in which said connector unit is heat sealed to said shaft along the forward margin of said signal balloon.

* * * * *